United States Patent [19]

Russo

[11] Patent Number: 4,610,673

[45] Date of Patent: Sep. 9, 1986

[54] GASTROENTERIC FEEDING TUBE

[75] Inventor: Ronald D. Russo, Barrington, R.I.

[73] Assignee: Superior Healthcare Group, Inc., Cumberland, R.I.

[21] Appl. No.: 703,319

[22] Filed: Feb. 19, 1985

[51] Int. Cl.[4] .......... A61M 31/005

[52] U.S. Cl. .......... 604/270

[58] Field of Search .......... 604/265, 270, 285, 275

[56] References Cited

U.S. PATENT DOCUMENTS

| | | | |
|---|---|---|---|
| 1,736,182 | 11/1929 | Wilkins | 604/270 |
| 4,249,535 | 2/1981 | Hargest, III | 604/265 |
| 4,390,017 | 6/1983 | Harrison et al. | 604/275 |
| 4,410,320 | 10/1983 | Dykstra et al. | 604/270 |
| 4,516,970 | 5/1985 | Kaufman et al. | 604/270 |
| 4,547,192 | 10/1985 | Brodsky | 604/270 |

OTHER PUBLICATIONS

Saltzberg et al., "Feeding Tube-Induced Pneumothorax", in *Journal of Parenteral and Enteral Nutrition*, vol. 8, No. 6, 1984, pp. 714-716.

Valentine et al., "Pleural Complications of Nasoenteric Feeding Tubes", in Journal of Parenteral and Enteral Nutrition, vol. 9, No. 5, 1985, pp. 605-607.

*Primary Examiner*—C. Fred Rosenbaum
*Assistant Examiner*—Jerome R. Smith, Jr.
*Attorney, Agent, or Firm*—Salter & Michaelson

[57] ABSTRACT

A gastroenteric feeding tube comprises a tubular shaft having distal and proximal ends, an enlarged intermediate portion which extends from the distal end of the shaft, and a weighted bolus which extends from the intermediate portion. The shaft has an imperforate sidewall and a side aperture in the intermediate portion communicates with the interior of the shaft for dispensing a feeding formula from the tube. The feeding tube is constructed so that it is sufficiently flexible to permit the passage thereof through a nostril of a patient during intubation of the tube, but nevertheless sufficiently rigid to permit the intubation of the tube without the use of a stylet therein.

6 Claims, 3 Drawing Figures

GASTROENTERIC FEEDING TUBE

BACKGROUND AND SUMMARY OF THE INVENTION

The instant invention relates to medical equipment, and more particularly to a gastroenteric feeding tube for the enteral feeding of a patient by tube.

The use of tubes for the enteral feeding of patients is widely accepted in medical practice. In most instances, enteral feeding is accomplished through the use of a gastroenteric feeding tube which is installed in a patient so that it extends through a nostril, through the esophagus, into the stomach and sometimes into the jejunum area of the intestines of the patient. Generally, it has been found that once a feeding tube has been installed in a patient in this manner, it can be maintained in the patient for up to a month or more and it can be utilized throughout this period for effecting nutritional feeding of the patient at regular intervals. In this regard, it has been found that generally enteric feeding can provide substantially more nutritional feeding of hospitalized patients than other artificial feeding methods, such as intravenous feeding. In fact, it has been found that gastroenteric feeding is generally preferable for both medical and nutritional reasons and that the malnutrition and weight loss effects which often occur when other types of artificial feeding methods are utilized for prolonged periods of time can often be avoided with gastroenteric feeding.

Generally, most of the heretofore available gastroenteric feeding tubes have comprised elongated tubular members having distal and proximal ends and having apertures therein adjacent the distal ends thereof, and weighted bolus portions which are secured on the distal ends of the tubular members thereof. Feeding tubes have generally been constructed of materials, such as silicone, having flexibilities which are sufficient to enable them to be passed through the nostrils of patients and obviously both the bolus and tubular portions of the heretofore available gastroenteric feeding tubes have been dimensioned to be received through the nostrils of patients without causing significant trauma. Further, many of the heretofore available feeding tubes have been formed with longitudinally extending X-ray opaque stripes thereon so that it can be easily determined whether or not they are properly installed in patients. The weighted bolus sections of tubes of this general type have been provided in order to prevent the distal ends of the tubes from being either partially or completely expelled from the stomachs of patients as a result of regurgitation. It has been found that this feature is particularly important since it is possible for the distal end of a feeding tube to be passed into a lung of a patient if it is expelled from the patient's stomach by regurgitation and this can cause feeding formula to be introduced into the patient's lung. Obviously therefore, it is extremely important that a feeding tube include a bolus section which has sufficient weight to maintain the tube in properly installed relation in a patient. Generally, it has been found that it is preferable for a feeding tube of this type to be installed in a patient so that the distal end of the tube is disposed in the jejunum area of the patient's intestines which is located just past the patient's pyloric valve. In this regard, generally it has been found that when a feeding tube is installed in a patient in this manner, highly effective and nutritional feeding of the patient can be accomplished, and it has also been found that the risk that the tube will be partially or completely expelled by regurgitation is substantially reduced.

Most of the heretofore available feeding tubes have generally been too flexible to permit their installation in patients without the use of some means for increasing their rigidity. This is because the tubular members of most feeding tubes have generally been constructed of highly flexible materials, such as silicone rubber, in order to minimize patient discomfort and also because the tubular members of most feeding tubes have had apertures therein adjacent the distal ends thereof which have made them extremely succeptible to collapsing and kinking. For these reasons, heretofore it has generally been the practice to intubate feeding tubes in patients using temporary wire or nylon stylets in the tubular members thereof to provide increased rigidity therein. While the use of stylets has proven to be an effective method of installing feeding tubes in patients, it has been found to have some very serious disadvantages. Specifically, because feeding tubes necessarily have apertures therein adjacent the distal ends thereof for passing feeding formula to patients, when a stylet is used to install a feeding tube in a patient, it is possible for the distal end of the stylet to inadvertently pass through one of the apertures in the tube and cause substantial damage to or even puncture a wall of the patient's esophagus, stomach or intestines. This can result in extremely serious injury to the patient and sometimes can even result in death. Hence, the installations of feeding tubes in patients have often involved substantial risks to the patients, and it has generally not been the practice for a nurse or technician to be permitted to install a feeding tube in a patient without the supervision of a doctor.

The instant invention provides an enteric feeding tube which can be effectively installed in a patient without the use of a stylet so that the risks associated with the installation of the tube are substantially reduced. The feeding tube of the instant invention comprises an elongated tubular member or shaft having distal and proximal ends, an enlarged intermediate portion which extends from the distal end of the shaft and an enlarged weighted bolus which extends from the intermediate portion. In contrast to most of the heretofore known feeding tubes, the tubular shaft of the feeding tube of the instant invention has an imperforate side wall. A lumen extends longitudinally through the tubular shaft, and instead of communicating with the exterior of the tube through side apertures in the shaft, it extends to the intermediate portion and communicates with a side aperture in the intermediate portion for passing feeding formula to a patient. Hence, the distal end of the tubular shaft is not prone to kinking or collapsing, and since the intermediate portion is formed with an enlarged sectional dimension, it is inherently more rigid than the shaft and it also is not prone to collapsing or kinking, even though it has a side aperture therein. The weighted bolus of the feeding tube is formed with a weight therein which is sufficient to maintain the bolus, the intermediate portion and the distal end of the shaft in the stomach or jejunum area of a patient, and the bolus is formed so that it has sufficient flexibility to permit the passage thereof through a nostril of a patient during the installation of the tube in the patient. The shaft and the intermediate portion are formed so that they have sufficient flexibility to permit their passage through a nostril of a patient during the installation of the tube in the patient, but so that they nevertheless have sufficient rigidity to permit the installation of the tube in the patient without the use of a stylet in the shaft. The intermediate portion of the tube is preferably formed with an open interior passage which extends from the lumen of the shaft to the side aperture in the intermediate portion and the passage and the side aperture preferably each have cross-sectional areas which are at least as great as the cross-sectional area of the lumen in the tubular shaft to permit the side aperture in the intermediate portion to be effectively utilized for dispensing a feeding formula into the stomach or intestines of a patient. The passage in the intermediate portion preferably terminates adjacent the portion of the side aperture therein which is closest to the bolus so that it does not leave a "dead space" in the distal end of the passage in the intermediate portion which would tend to collect feeding formula and become clogged. The intermediate portion is formed with a greater sectional dimension than the tubular shaft of the feeding tube so that it is resistant to kinking or collapsing, despite the fact that the intermediate portion has at least one side aperture therein, and the bolus preferably has substantially the same cross-sectional dimension as the intermediate portion. The shaft of the feeding tube preferably has a sectional dimension of between 0.08 and 0.16 inches, a wall thickness of between 0.015 and 0.035 inches, and the lumen in the tubular shaft preferably has a sectional dimension of at least 0.05 inches. The shaft is preferably made of a material having an A Durometer Scale hardness of between 60 and 100. The intermediate portion which extends from the tubular shaft is preferably formed so that it is at least as rigid as the shaft, and the intermediate portion is preferably made of a material having an A Durometer Scale hardness of between 50 and 100. The bolus preferably comprises a casing portion and weight means in the casing portion, and the casing portion is preferably made of a material having an A Durometer Scale hardness of between 45 and 90. Preferably, the shaft, the intermediate portion, and the casing portion of the bolus are made of a polyether based polyurethane, since it has been found that the components of the feeding tube can easily be made so that they have the desired degrees of stiffness from a compound of this type, and it has also been found that a polyether based polyurethane generally maintains its flexibility, even after prolonged exposure to gastric mucosa.

Accordingly, it is seen that the feeding tube of the instant invention has substantial advantages over the heretofore available feeding tubes. Specifically, because the feeding tube is constructed so that the side apertures therein, which are provided for passing a feeding formula into the stomach or intestines of a patient extend, through the enlarged intermediate portion rather than through the wall of the distal end portion of the tubular shaft, the distal end portion of the shaft is substantially less prone to collapsing and kinking during the installation of the tube in a patient. Further, because the intermediate portion is constructed in an enlarged dimension, kinking of the intermediate portion is not normally a problem during the installation of the tube in a patient, despite the fact that the intermediate portion has at least one side aperture therethrough. Because of these features and because of the stiffnesses of the components of the tube as hereinabove specified, the feeding tube can be installed in a patient without the use of a stylet. Further, because of the stiffnesses of the components of the tube, the feeding tube can be installed in a patient without causing a significant degree of trauma to the patient, and because the feeding tube is constructed of a polyether based polyurethane, it can be left in a patient for a prolonged period of time without causing irritation to the patient.

Feeding tubes representing the closest prior art to the instant invention of which the applicant is aware are disclosed in the U.S. Pat. Nos. to Wilkins, No. 1,736,182, Dykstra et al, No. 4,410,320, and Harrison et al, No. 4,390,017, and in the copending U.S. application to Brodsky, Ser. No. 484,413. However, since none of the devices disclosed in these references embody the novel features of the feeding tube of the instant invention which enable it to be intubated in a patient without the use of a stylet, they are believed to be of only general interest.

Accordingly, it is a primary object of the instant invention to provide a gastroenteric feeding tube which can be installed in a patient without the use of a stylet.

Another object of the instant invention is to provide a feeding tube which can be installed in a patient with a minimum of risk to the patient.

As even further object of the instant invention is to provide an effective gastroenteric feeding tube which can be installed in a patient by a nurse or a technician without the supervision of a physician.

Other objects, features and advantages of the invention shall become apparent as the description thereof proceeds when considered in connection with the accompanying illustrative drawings.

DESCRIPTION OF THE DRAWING

In the drawing which illustrates the best mode presently contemplated for carrying out the present invention.

DESCRIPTION OF THE INVENTION

Figure 1:
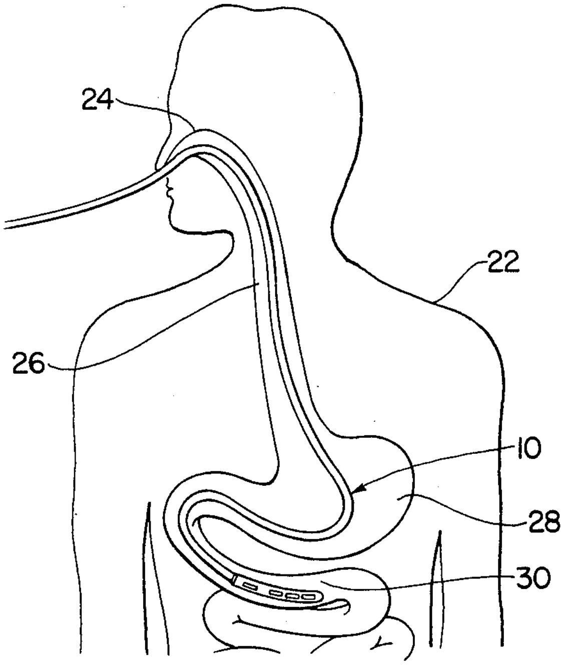
FIG. 1 is a schematic view of the feeding tube of the instant invention installed in a patient.
Figure 2:
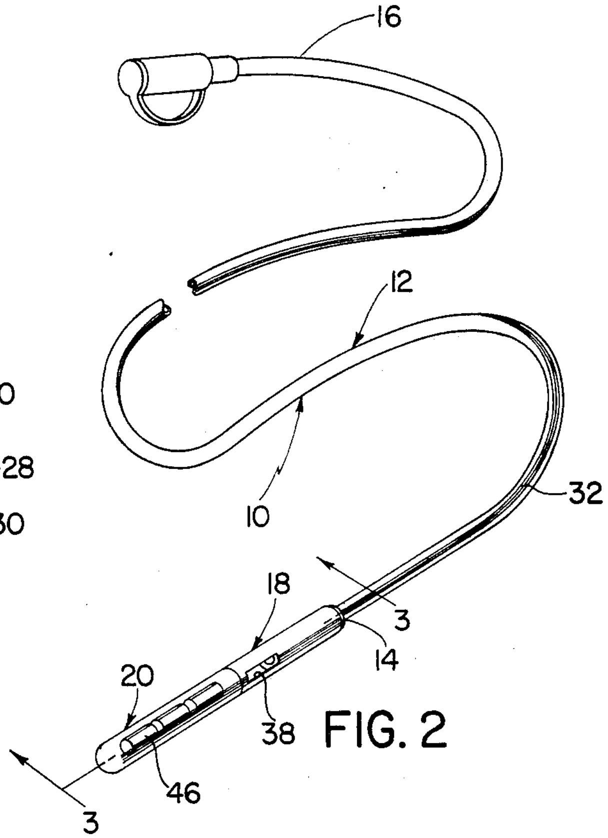
FIG. 2 is a perspective view of the feeding tube.
Figure 3:
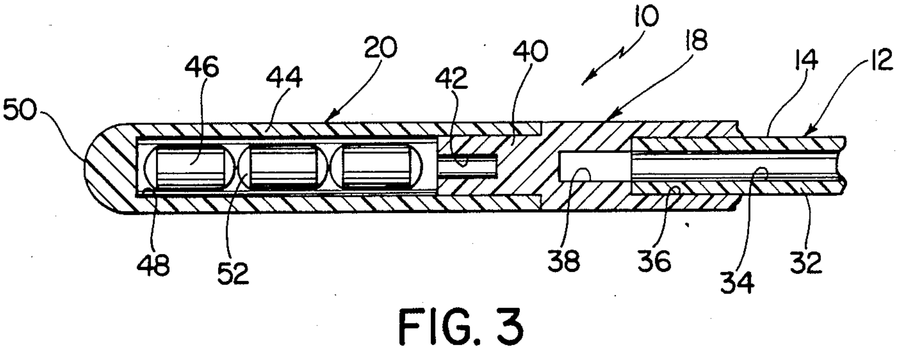
FIG. 3 is an enlarged sectional view taken along line 3—3 in FIG. 2.

Referring now to the drawing, the feeding tube of the instant invention is illustrated and generally indicated at 10 in FIGS. 1 through 3. The feeding tube 10 comprises an elongated tubular shaft portion generally indicated at 12 having distal and proximal ends 14 and 16, respectively, an enlarged intermediate portion generally indicated at 18 which extends from the distal end 14 of the shaft 12, and a weighted bolus generally indicated at 20 which extends from the intermediate portion 18. As illustrated in FIG. 1, the feeding tube 10 is adapted to be installed or intubated into a patient 22 so that it extends through the nasal pharynx 24, through the esophagus 26, into the stomach 28, and sometimes into the jejunum area 30 of the intestines of the patient which is just past the pyloric valve (not shown). Accordingly, the feeding tube 10 can be effectively utilized for introducing a feeding formula into the stomach 28 or the jejunum area 30, depending on the manner in which the tube has been installed, to provide nutritional feeding of the patient 22 over a prolonged period of time.

The tubular shaft 12 comprises an elongated tubular member having an imperforate outer wall 32 and a lumen 34 extends longitudinally through the shaft 12. The shaft 12 is constructed so that it has sufficient flexibility to permit the passage thereof through a nostril of a patient during the intubation of the tube 10 in the patient, but so that it nevertheless has sufficient rigidity to permit the intubation of the tube without the use of a stylet in the lumen 34. Specifically, the shaft 12 is preferably constructed of a material having an A Durometer Scale hardness of between 45 and 90, and it preferably has a cross-sectional dimension of between 0.080 and 0.160 inches. Further, the shaft 12 is preferably constructed so that the thickness of the wall 32 is between 0.015 and 0.035 inches and so that the lumen 34 has a sectional dimension of at least 0.05 inches. Preferably, the shaft is constructed of a polyether based polyurethane so that it is substantially unaffected by gastric mucosa in the stomach of the patient, even when the tube 10 is left in the patient for a period of up to a month.

The intermediate portion 18 is received and secured on the distal end 14 of the shaft 12, and it is constructed with an enlarged sectional dimension with respect to the shaft 12. The intermediate portion 18 is formed with a socket 36 therein and the distal end portion of the shaft 12 is received in the socket 36 and secured therein with a suitable adhesive. In this regard, however, other embodiments of the feeding tube of the instant invention wherein the shaft 12 and the intermediate portion 18 are integrally formed are also contemplated. The intermediate portion 18 is formed with a transverse slot 38 therein which communicates with the lumen 34 and defines an inner passage and a pair of side apertures in the intermediate portion for passing feeding formula from the lumen 34 to the exterior of the tube 10. The cross-sectional area of the slot 38 is preferably at least as great as the cross-sectional area of the lumen 34 to permit the unrestricted flow of feeding formula from the lumen 34 through the slot 38. Preferably, the portion of the interior passage in the intermediate portion 18 which is closest to the bolus 20 is adjacent the portions of the apertures defined by the slot 38 which are closest to the bolus 20 so that a dead space is not formed in the interior of the intermediate portion 18. The intermediate portion 18 is preferably constructed so that it is at least as rigid as the shaft 12 and it is constructed so that it is sufficiently flexible to permit the passage thereof through a nostril of a patient during the installation of the tube 10 in the patient, but nevertheless sufficiently rigid to permit the installation of the tube 10 in the patient without the use of the stylet. Preferably, the intermediate portion 18 is constructed of a polyether based polyurethane having an A Durometer Scale hardness of between 50 and 100. The intermediate portion 18 has an enlarged sectional dimension with respect to the shaft 12 to make it resistant to collapsing or kinking, although it obviously must be dimensioned to be passed through a nostril of a patient. The end of the intermediate portion 18, which is opposite from the shaft 12, is formed as a cylindrical plug 40 for receiving the bolus 20, the plug 40 having an axial bore 42 of reduced extent therein for providing increased flexibility in the intermediate portion 18 and for facilitating the manufacture thereof by molding.

The bolus 20 comprises an outer casing portion 44 and a plurality of weight elements 46 which are received and contained in the casing portion 44. The casing portion 44 is preferably made of a polyether based polyurethane, and it preferably has substantially the same cross-sectional dimension as the intermediate portion 18. The casing portion 44 is preferably received and secured on the plug portion 40 of the intermediate portion 18 with a suitable adhesive and it preferably forms a generally smooth extension of the intermediate portion 18. A substantially axial bore 48 is provided in the casing portion 44 for receiving and containing the weight elements 46 and the casing portion 44 preferably terminates in a substantially rounded end 50. The weight elements 46 are preferably made of a suitable corrosion resistant non toxic metal, such as stainless steel, so that they would not cause significant injury to a patient in the event of a rupture in the casing portion 44. Further, the weight elements 46 are preferably formed with rounded ends 52 so that they do not bind on each other when the bolus 20 is flexed or bent, and they are preferably formed in reduced lengths so that they do not substantially restrict the flexibility of the bolus 20. The casing portion 44 of the bolus 20 is preferably made of a material having an A Durometer Scale hardness of between 45 and 90, and it is preferably made of a polyether based polyurethane. Further, although in the tube 10 as herein set forth, the bolus 20 and the intermediate portion 18 are formed as separate components, other embodiments of the feeding tube of the instant invention wherein the bolus and the intermediate portion are integrally formed are contemplated.

For use of the tube 10, it is installed in a patient, such as the patient 22, in the manner hereinabove set forth. In this regard, however, because the side wall 32 is imperforate, and because the tube 10 has a somewhat higher degree of rigidity than the heretofore known feeding tubes, the tube 10 can be installed in the patient 22 without the use of a stylet in the lumen 34. In this regard, since the tube 10 is constructed of a polyether based polyurethane, the hardness or stiffness of the tube 10 is not increased significantly by prolonged exposure to gastric mucosa and therefore the tube can be constructed with a slightly higher degree of stiffness without significantly affecting the ultimate patient comfort. Because the slot 38 is formed in the enlarged intermediate portion 18, and because the intermediate portion 18 is preferably at least as rigid as the shaft 12, the intermediate portion 18 also does not tend to kink or collapse when the tube 10 is installed without the use of a stylet. Further, because the slot 38 also defines the end of the open interior portion of the tube 10, the tube 10 does not have an interior area of "dead space" where feeding formula could collect or solidify, and because the area of the apertures defined by the slot 38 is at least as great as the sectional area of the lumen 34, the slot 38 provides little or no resistance to the flow of feeding formula through the tube 10.

Accordingly, it is seen that the feeding tube of the instant invention has substantial advantages over the heretofore known feeding tubes. Specifically, the feeding tube 10 can be intubated in a patient without the use of a stylet, and hence, it can be intubated with substantially less risk to the patient. This makes the feeding tube substantially more practical for many applications and it also makes it practical for the feeding tube to be installed in a patient by a nurse or technician without the supervision of a physician in many cases. Further, the feeding tube is constructed so that it can be effectively installed in a patient, without causing substantial trauma to the patient and it can remain in the patient for a prolonged period of time without causing irritation. Hence, for these reasons as well as the other reasons hereinabove set forth, it is seen that the feeding tube of the instant invention represents a significant advancement in the medical art which has substantial merit from both medical and commercial standpoints.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A gastroenteric feeding tube comprising an elongated tubular shaft having distal and proximal ends and having a longitudinally extending lumen therethrough, an enlarged intermediate portion which extends from the distal end of said shaft, and a weighted bolus which extends from said intermediate portion, said intermediate portion having at least one side aperture therein which communicates with said shaft lumen, said bolus being sufficiently flexible to permit the passage thereof through a nostril of a patient during the installation of said tube in said patient, said shaft having an imperforate side wall, said shaft having a sectional dimension of between 0.080 and 0.160 inches, and a wall thickness of between 0.015 and 0.035 inches, said lumen having a sectional dimension of at least 0.05 inches, said shaft being made of a material having an A Durometer Scale hardness of between 60 and 100, said intermediate portion being at least as rigid as said shaft, whereby said shaft and said intermediate portion are sufficiently flexible to permit the passage thereof through said nostril during the installation of said tube in said patient, but nevertheless sufficiently rigid to permit the installation of said tube in said patient without the use of a stylet.

2. In the feeding tube of claim 1, the total crosssectional area of said at least one aperture in said intermediate portion being at least as great as the cross-sectional area of said lumen.

3. In the feeding tube of claim 1, said intermediate portion having an open passage therein which provides communication between said lumen and said at least one aperture in said intermediate portion, the closest portion of said passage to said bolus being adjacent the closest portion of said at least one aperture to said bolus.

4. In the feeding tube of claim 1, said bolus and said intermediate portion being of substantially the same crosssectional dimension.

5. In the feeding tube of claim 1, said bolus comprising a casing portion and weight means in said casing portion, said casing portion being made of a material having an A Durometer Scale hardness of between 45 and 90, said intermediate portion being made of a material having an A Durometer Scale hardness of between 50 and 100.

6. In the feeding tube of claim 1, said shaft being made of a polyether based polyurethane.

* * * * *